US006451548B1

(12) United States Patent
Andersson et al.

(10) Patent No.: US 6,451,548 B1
(45) Date of Patent: Sep. 17, 2002

(54) METHODS FOR SCREENING FOR SPECIFIC INHIBITORS OF TRAP AND IDENTIFYING COMPOUNDS FOR TREATMENT OF DISEASES OR CONDITIONS RESULTING IN INCREASED BONE RESORPTION USING ACTIVATED TRAP

(75) Inventors: Göran Andersson, Huddinge; Barbro Ek-Rylander, Enskede; Cornelia Oellig, Järfälla, all of (SE)

(73) Assignee: Biovitrum AB, Stockholm (SE)

( * ) Notice: Subject to any disclaimer, the term of this patent is extended or adjusted under 35 U.S.C. 154(b) by 0 days.

(21) Appl. No.: 09/442,816

(22) Filed: Nov. 18, 1999

Related U.S. Application Data
(60) Provisional application No. 60/110,354, filed on Dec. 1, 1998.

(30) Foreign Application Priority Data

Nov. 19, 1998 (SE) ................................................ 9803959

(51) Int. Cl.[7] .............................................. C12Q 1/42
(52) U.S. Cl. ................................ 435/21; 4/195; 4/212; 4/219
(58) Field of Search .......................... 435/21, 195, 212, 435/4, 219

(56) References Cited

PUBLICATIONS

Marshall et al. Recombinant human and mouse purple acid phosphatases: expression and characterization. Archives of Biochemistry and Biophysics. Sep. 15, 1997, vol. 345, pp. 230–236.*
Orlando et al. Purification and properties of the native form of the purple acid phosphatase from bovine spleen. Biochemistry. Aug. 17, 1993, vol. 32, pp. 8120–8129.*
Schneyer. Calcitonin and the treatment of osteoporosis. Md Med J. Jun. 1991, vol. 40, pp. 469–473.*
Zheng et al. Tartrate resistant acid phosphatase activity in rat cultured osteoclasts is inhibited by a carboxyl terminal peptide (osteostatin) from parathyroidhormone–related protein. Journal of Cellular Biochemistry. Feb. 1994, vol. 54, pp. 145–153.*
Vincent et al. An enzyme wth a double identity: purple acid phosphatase and tartrate–resistant acid phosphatase. FASEB J. Sep. 1990, vol. 4, pp. 3009–3014.*
Allen et al, *Journal of Bone and Mineral Research*, 4(1):47–55 (1989).
Dialog Medline Abstract of Zaidi et al, *Biochem. Biophys. Res. Commun.*, 159(1):68–71 (1989).
STN International Abstract of Chemical Abstract No. 121:50499 of *J. Cell. Biochem.*, 54(2):145–53 (1994).
Dialog Medline Abstract of Weir et al, *Journal of Bone and Mineral Research*, 11(10):1474–81 (1996).
Dialog Medline Abstract of Quinn et al, *Calcis. Tissue Int.*, 60(1):63–70 (1997).
Dialog Medline Abstract of Berghuis et al, *Eur. J. Orthod.*, 16(2):130–37 (1994).
Dialog Medline Abstract of Hara et al, *Bone*, 16(2):179–84 (1995).
Ljusberg et al, *Biochem. J.*, 343:63–69 (1999).
Rodan et al, *Science*, 289:1508–1514 (2000).
*Drug Report*, Hypercalcemia, Osteoporosis, Pagets Disease (Apr. 25, 2001).
*Drug Report*, Osteoporosis, Pagets Disease (May 2, 2001).
Ek–Rylander et al, *The Journal of Biological Chemistry*, 266(36):24864–24869 (1991).
Primer on the Metabolic Bone Diseases ad Disorders of Mineral Meabsolism, 2nd Edition, Editor, Murray J. Favus, M.D., Raven Press, New York (1993): Chapter 5—Mundy, *Bone Resorbing Cells*, pp. 25–32.
Primer on the Metabolic Diseases and Disorders of Mineral Meabsolism, 2nd Edition, Editor, Murray J. Favus, M.D., Raven Press, New York (1993): Section V, Chapter 65—Klein, *Nutritional Rickets and Osteomalacia*, pp. 264–290.
Primer on the Metabolic Bone Diseases and Disorders of Mineral Meabsolism, 2nd Edition, Editor, Murray J. Favus, M.D., Raven Press, New York (1999): Chapter 4—Mundy, *Bone Remodeling*, pp. 30–38.
GenBank Sequence NM_001611.
GenBank Sequence NM_019144.
"Clustal W" Sequence Listing.

* cited by examiner

*Primary Examiner*—Nashaat T. Nashed
*Assistant Examiner*—Christian L. Fronda
(74) *Attorney, Agent, or Firm*—Fish & Richardson P.C.

(57) ABSTRACT

The invention relates to the use of activated TRAP (tartrate-resistant and purple acid phosphatases) for screening for specific inhibitor of TRAP activity useful in the treatment of diseases or degenerative conditions resulting in increased bone resorption, such as tissue damages, bone metabolic disorders, osteoporosis. TRAP can be activated by proteolytic activation of TRAP e.g. by cleaving with a protease, papain-like enzyme.

16 Claims, 4 Drawing Sheets

Figure 1:
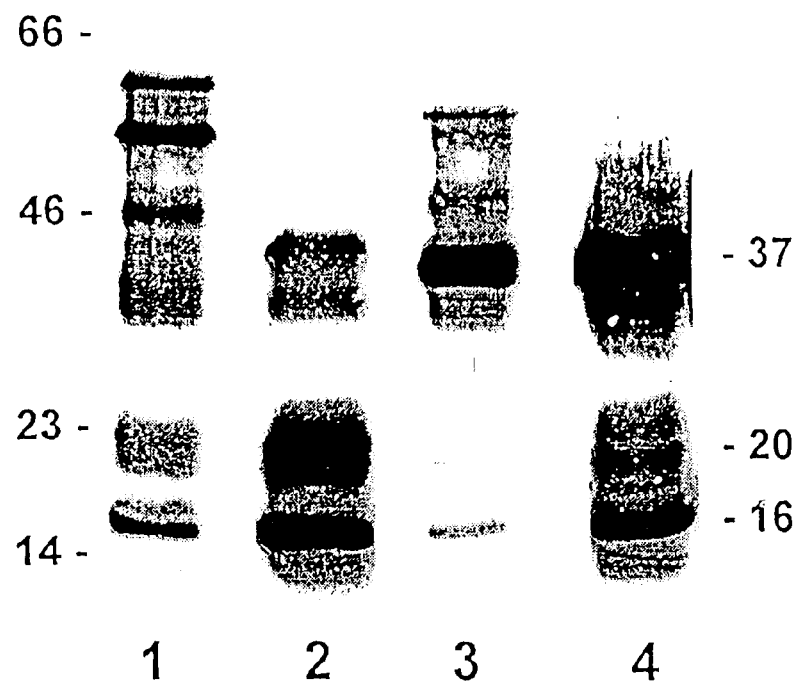

METHODS FOR SCREENING FOR SPECIFIC INHIBITORS OF TRAP AND IDENTIFYING COMPOUNDS FOR TREATMENT OF DISEASES OR CONDITIONS RESULTING IN INCREASED BONE RESORPTION USING ACTIVATED TRAP

This application claims priority from Swedish Patent Application No. 9803959-7, filed Nov. 19, 1998, and U.S. Provisional Patent Serial No. 60/110,354, filed Dec. 1, 1998. These applications are incorporated herein by reference in their entirety.

The invention relates to the use of activated recombinant TRAP (tartrate-resistant and purple acid phosphatases) for screening for specific inhibitor of TRAP activity useful in the treatment of diseases or degenerative conditions resulting in increased bone resorption, such as tissue damages, bone metabolic disorders, osteoporosis.

TRAP can be activated by proteolytic activation of TRAP e.g. by cleaving with a protease, papain-like enzyme.

BACKGROUND

Normal bone function requires a turnover of bone. Bone is constantly being rebuilt by cycles of resorption and formation which means that formation is closely linked to resorption (a phenomenon referred to as coupling).

TRAP is an enzyme expressed predominantly in bone resorbing cells (osteoclasts). Investigations in TRAP knock-out mice show that the resorption process is disrupted so that, with increasing age, TRAP knockout mice become osteopetrotic, i.e. have an increased bone mineral content and more dense bone is formed. Osteoclasts prepared from these animals are functional and do resorb bone but to a lesser extent than wild type mouse osteoclasts.

Phosphatases are enzymes that remove organic phosphates from proteins. The mammalian Purple Acid Phosphatases (PAPs), a group of enzymes to which Tartrate Resistant and purple Acid Phosphatase (TRAP) belongs, are characterized by a binuclear iron center at the active site. Purple acid phosphatases (PAPs) are acid metallohydrolases that contain a binuclear $Fe^{3+}M^{2+}$ center in their active site, where M=Fe or Zn [1–3]. In mammals, these enzymes are also referred to as tartrate-resistant acid phosphatases (TRAPs) (EC 3.1.3.2) or type 5 acid phosphatases [4]. TRAPs are iron-containing, monomeric glycoproteins with molecular weights of around 35,000 Da [5]. The deduced amino acid sequences of human, rat and mouse TRAPs show a high degree of homology with the mammalian members of the PAP family, e.g uteroferrin (Uf) and bovine spleen PAP [6–9]. Recently, EPR spectroscopic analysis of rat recombinant TRAP [10] has provided compelling evidence that this enzyme also belongs to the PAP family.

Mammalian PAPs contain a FeFe center, while a plant PAP from red kidney beans (KBPAP) instead has a FeZn center [11]. Moreover, the mammalian protein phosphatases calcineurin (type 2B) [12] and protein phosphatase type 1 (PP-1) [13] both contain a di-nuclear metal centre and also reveal a striking similarity to the plant PAP enzyme in the coordination environment of the active site, except for the absence of the tyrosine ligand. PP-1 and calcineurin are serine/threonine protein phosphatases, suggesting that also PAPs may function as protein phosphatases. It has been shown that PAP enzymes exhibit a rather broad specificity as these enzymes can dephosphorylate both serine- and tyrosine-bound phosphate moieties in phosphoproteins [10, 14–19].

The binuclear iron center, low pH optimum (≈5), high isoelectric point (≈9) and insensitivity to inhibition by L(+) tartrate are features of TRAP that may be involved in the apparent substrate specificity at the low pH in the osteoclastic resorption area. The TRAP enzyme is a cationic glycoprotein with a molecular mass of 35 kD and a monomeric 325 amino acid peptide structure. The peptide sequence of rat bone TRAP displays 89–94% homology to TRAP enzyme of the human placenta, bovine spleen, and uteroferrin. TRAP hydrolyzes aryl phosphates, nucleoside di- and triphosphates, pyrophosphate and phosphoproteins. Its physiological role remains unclear but TRAP may mediate dephosphorylation of bone matrix proteins such as osteopontin and bone sialoprotein.

Dephosphorylation of bone matrix proteins enables osteoclasts to migrate over the bone surface and TRAP is therefore likely to be involved in the attachment of osteoclasts to the bone surface.

In humans and rats, PAP enzymes are highly expressed in certain cells of the monocyte-macrophage lineage, such as the bone-resorbing osteoclasts and certain activated macrophages in spleen, liver and lung [20–23], and TRAP has since long been used as a histochemical marker for these cells. Given the broad substrate specificity of PAP enzymes, it is conceivable that other factors, such as local availability and proper compartmentalisation of PAPs with their potential substrates, are other important factors in determining the physiological action of PAPs in biological systems.

The cDNA sequences of TRAP/PAP enzymes from different species and organs all indicate that these enzymes are translated as a single polypeptide of around 35 kDa [7–9, 24]. This contrasts with the predominantly two subunit structure, consisting of a 20–23 kDa N-terminal domain linked through a disulphide bond to a 15–17 kDa C-terminal domain, observed in purified enzyme preparations from a variety of sources including human and rat bone [25, 26], giant cell tumors [27] and normal and pathological spleen [28–30]. In contrast, uteroferrin purified from endometrial secretions are mostly in the single subunit form [28, 31] as are the recombinant PAPs generated by overexpression using the Baculovirus system [10, 17, 32]. Orlando et al [29] managed to separate the monomeric and two-subunit variants of PAP from bovine spleen, and demonstrated a markedly higher specific enzyme activity associated with the two subunit form. Moreover, digestion of the single subunit form with the serine proteases trypsin or chymotrypsin generated the 23 kIDa and 15 kDa disulfide-linked fragments characteristic of the two subunit form together with a significant enhancement of enzyme activity. Similar nicking and activation of the non-cleaved purified recombinant human and mouse PAPs were noted upon prolonged storage [17].

Inhibitors of TRAP are known, such as PGE2 [Quinn et al Calcif. Tissue Int (1997), 60 (1) 63–70], which has an influence on the formation of osteoclasts and thus reduce the amount of TRAP, hemin (ferric protoporphyrin) [Reddy et al, Blood (1996), 88 (6) 2288–2297], which regulates the TRAP on a gene level i.e. a lowering of the expression of TRAP and calcitonin which inhibits the release of TRAP. Calcitonin, has an effect against osteoclasts and is used as medicament against osteoporosis.

These known inhibitors are not specific (no direct inhibitor) and synthetic inhibitors for the protein and the enzyme activity can therefore not be used in vivo.

Current drugs on the market for treatment of osteoporosis turn off bone resorption. We now have found a possibility to modulate and lower the bone resorption rate, but not to turn it off completely.

THE INVENTION

The overall goal of this invention is to develop drugs for the treatment of osteoporosis. We have compared certain structural and enzyme kinetic properties of recombinant rat TRAP (single-subunit) with those of the native TRAP/TRAP enzyme (two-sub-unit), and examined the effects of cleaving the monomeric recombinant TRAP with the serine proteinase trypsin or the cysteine proteinase papain. Cysteine proteinases were chosen because enzymes belonging to this family appear to serve important roles in resorptive and degradative processes in cells of the monocyte-macrophage lineage [33–35].

The results show that the monomeric form of TRAP represents a latent proenzyme with low enzymatic activity towards both tyrosine- and serine-containing phosphosubstrates. We have found that members of the cystein proteinase family play an important role in degradative processes involving the TRAP enzymes by converting the TRAPs to enzymatically active and micro environmentally regulated species.

To our surprise, we found that cleavage with special proteases, such as papain, but not trypsin, significantly activate the enzyme and confer similar properties with regard to enzymatic parameters such as pH-dependence and sensitivity to reducing agents, as well as in size of the subunits and the site of initial proteolytic cleavage, as compared to the bone variant. Similar results were observed when cathepsin B was used instead of papain.

We have found that it is important to cleave at the right site and that not all proteases are giving an activated TRAP. The protease must be specifically selected to give the desired activated, useful TRAP.

We have also found that the rTRAP cannot be used when looking for inhibitors, which are regarded as crucial in the research for medicament against osteoporosis. We found that rTRAP must be processed before being activated and this activated (active) form of TRAP, aTRAP, is different from the earlier known rTRAP. aTRAP is a proteolytic modification of rTRAP.

The activity of aTRAP is about 10–20 times higher than for rTRAP.

The invention relates to the use of activated TRAP (tartrate-resistant and purple acid phosphatases) for screening for specific inhibitor of TRAP activity useful in the treatment of diseases or degenerative conditions resulting in increased bone resorption, such as tissue damages (e.g. inflammation, cancer), bone metabolic disorders, osteoporosis. TRAP can be activated by proteolytic activation of TRAP e.g. by cleaving with a protease, papain-like enzyme.

The scope of the present patent application is defined in the attached claims.

The recombinant activated TRAP can be used as a screening tool to identify specific inhibitors of this enzyme and to develop drugs for the treatment of osteoporosis. Using an inhibitor of activated TRAP, an enzyme expressed predominantly in bone, resorbing cells (osteoclasts) will modulate osteoclast activity. An up-regulated bone turnover rate in combination with an imbalance between bone resorption and formation are key elements in postmenopausal osteoporosis, and using a TRAP inhibitor in patients with high bone turnover rate in postmenopausal osteoporosis is likely to shift the net effect of bone turnover to bone anabolism.

Recombinant rat TRAP has been a necessary tool for High Throughput Screening (HTS) and the results of such HTS show that it can be performed for the intended purpose.

FIGURES

FIG. 1. Protein composition and immunoblot analysis of recombinant and bone TRAP.

Figure 2:
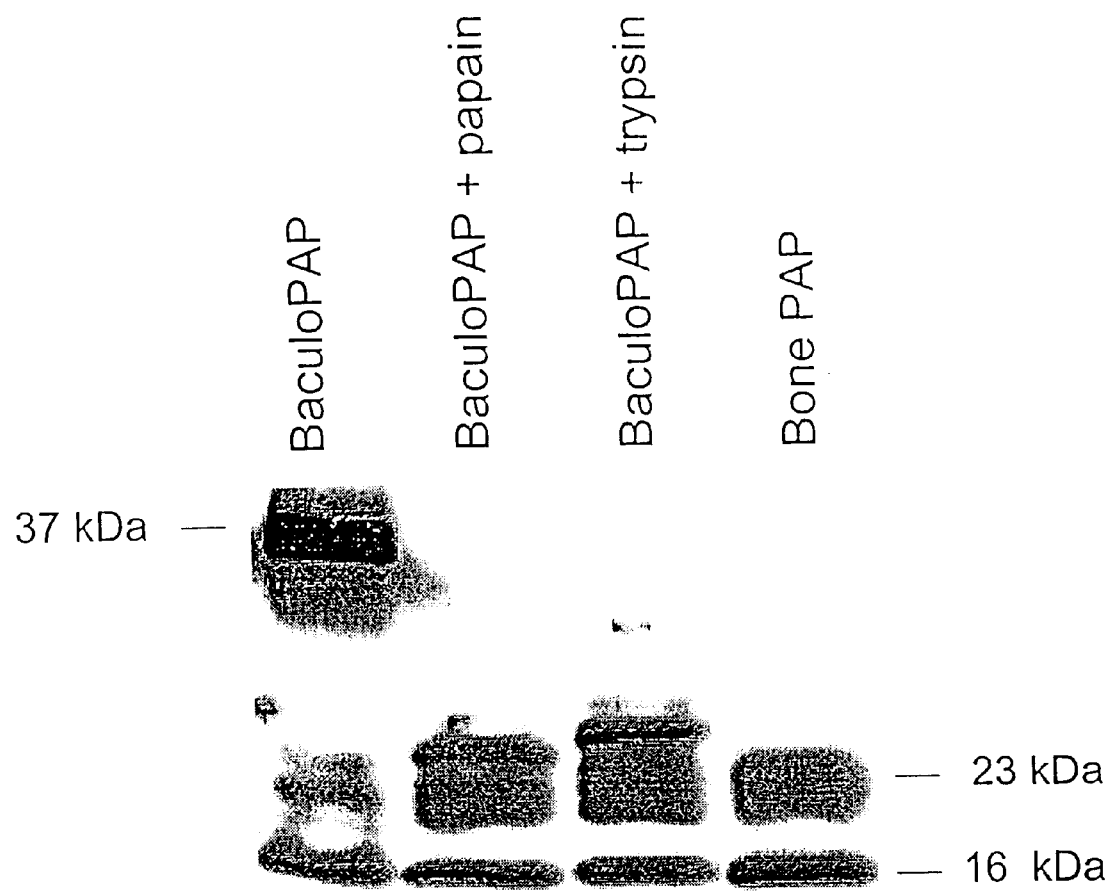

FIG. 2. Fragmentation pattern after proteolytic digestion of recombinant TRAP.

Figure 3:
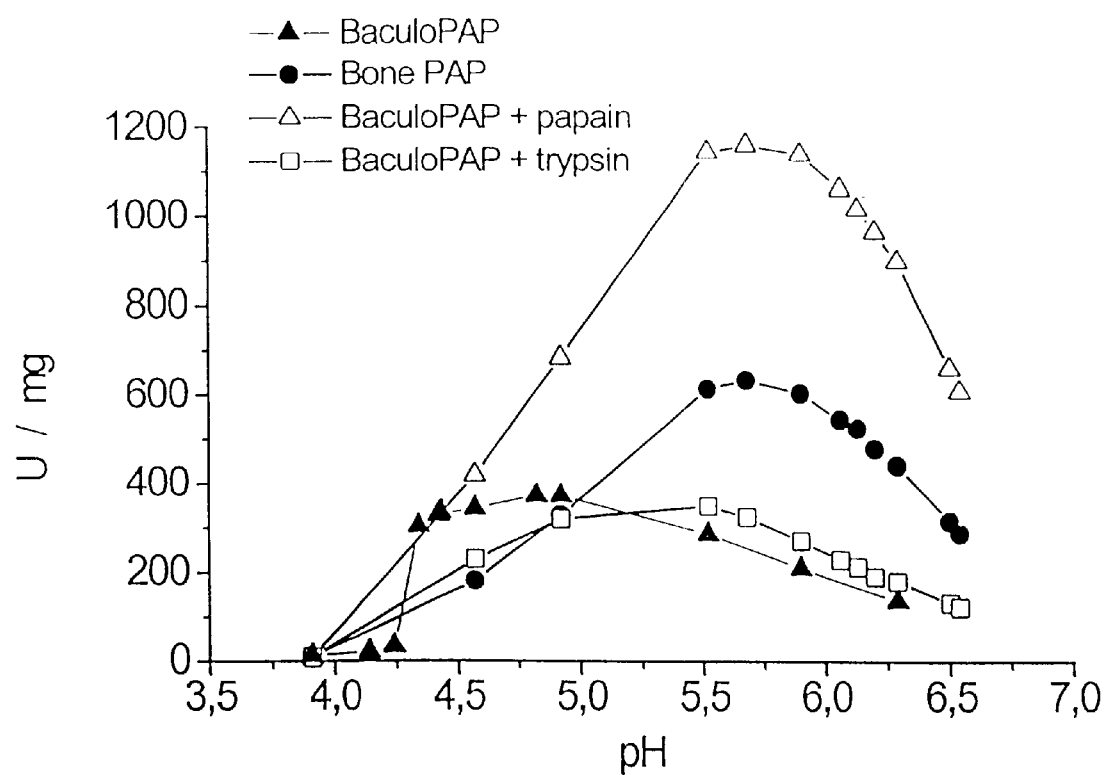

FIG. 3. pH-dependence for pNPP hydrolysis of intact and proteolytically cleaved TRAP.

Figure 4A:
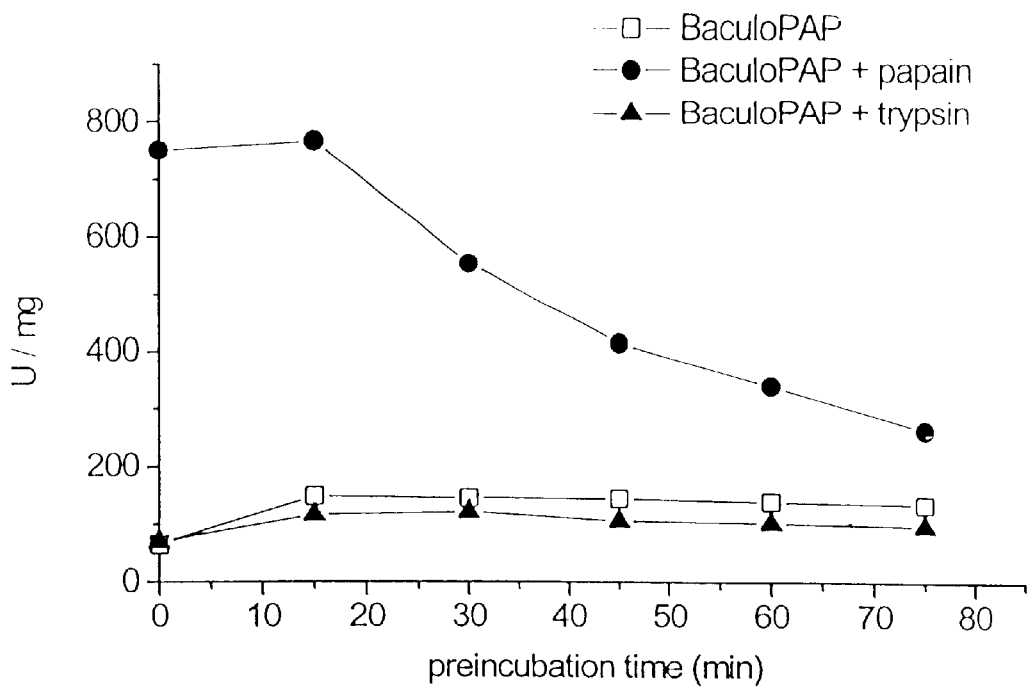

FIGS. 4a and b. Differential sensitivity of intact and proteolytically cleaved TRAP to reducing agents.

EXAMPLES

Materials and Methods

Phosphothreonine (pT), phosphoserine (pS), phosphotyrosine (pY) and p-nitrophenylphosphate (pNPP) were purchased from Sigma. The phosphopeptides RRA(pT)VA, END(pY)INASL and DADE(pY)LIPQQG came from Promega. FRI(pS)HELDS (F9S) and EDEE(PS)EDEE were synthesized by Neosystem Laboratoire, Strasbourg, France. Osteopontin (OPN) was purified from milk according to procedure described under Methods. DEAE-Sephacel and Phenyl-Sepharose CL-4B were purchased from Pharmacia Biotech, Sweden. Proteases and protease inhibitors were purchased from: Papain-agarose (Pierce), Trypsin-agarose (Sigma), cathepsin B (Anawa, Switzerland), protease inhibitor cocktail Complete, Pefabloc, pepstatin, E-64 from Boehringer Mannheim, Germany. Materials used for Western blot analysis were: immuno-PVDF membranes (Bio-Rad), colloidal gold (Bio-Rad), alkaline phosphatase- conjugated goat- anti rabbit IgG (Sigma), NBT/BCIP (nitrobluetetrazolium chloride/5-bromo-4-chloro-3-indolyl-phosphate p-toluidine salt; Bio-Rad).

Purification of TRAP

Recombinant TRAP, Baculovirus-produced recombinant TRAP (BaculoTRAP) was purified from the culture supernatant of recombinant Baculovirus-infected cells as described previously [10]. This preparation initially had a specific activity of 428 U/mg Bone TRAP was purified from the long bones of 40 3 week old Sprague Dawley rats. All operations were performed at 4° C. The dissected bones, free from soft tissue, were cut into small pieces and placed in homogenization solution with protease inhibitors (3 ml/g bone); 0.15 M KCl, 0.1% Triton X-100, Pefabloc (1 mg/ml), Pepstatin A (10 $\mu$g/ml), E-64 (10 $\mu$g/ml) and 5 mM EDTA. A Polytron homogenizer (Brinkman Instruments Westbury, N.Y.) was used for homogenization during 10 seconds, with 1 minute intervals, until a homogenous suspension was achieved. The homogenate was cleared by centrifugation at 3,200×g for 30 min. 5 % protamine sulfate was added dropwise to the supernatant during continous stirring to a final concentration of 0.5%, with further stirring for 30 min. The suspension was centrifuged for 30 min at 3,200×g and the supernatant was adjusted to pH 6.5. The supernatant was loaded onto CM cellulose column and subsequent purification steps were performed as previously described [10].

TRAP Activity Assays

P-nitrophenylphosphphatase activity was assayed in 96-well plates using the p-nitrophenylphosphate (pNPP) as substrate in the incubation medium (150 $\mu$l) containing (final concentrations); 10 mM pNPP, 0.1 M sodium acetate pH 5.8, 0.15 M KCl, 0.1% Triton X-100, 10 mM sodium tartrate, 1 mM ascorbic acid and 0.1 mM FeCl$_3$. The p-nitrophenol liberated after 1 hour of incubation at 37° C. was converted into p-nitrophenylate by the addition of 100 $\mu$l of 0.3 M NaOH, and the absorbance was read at 405 nm. For absorbance reading a Spectramax 250 spectrophotometer (Molecular Devices, Sunnyvale, Calif.) was used.

1 U of p-nitrophenylphosphatase activity corresponds to 1 μmole of p-nitrophenol liberated per minute at 37° C. Phosphatase assay with the substrates pT, pS, pY, RRA(pT)VA, END(pY)INASL, DADE(pY)LIPQQG, FRI(pS)HELDS, EDEE(pS)EDEE and OPN was performed essentially according to [37]. The substrates were dissolved in incubation medium containing the same buffer as in the pNPP-assay. After 1 hour of incubation (final volume 50 μl) at 37° C. the assay was stopped by addition of 50 μl of color reagens (0.12% Malachite-green in 3 M $H_2SO_4$/7.5% ammomium molybdate/11% Tween-20; 10:2.5:0.2). A phosphate standard curve (0–nmol) was always run in parallel. After color development for 10 min the absorbance at 630 nm was measured using a Spectramax 250 spectrophotometer.

Proteolytic Digestion of TRAP 25 μg baculoTRAP or bone TRAP were digested with 100 pl (0 7 units) papain-agarose in 500 μl of incubation solution; 10 mM sodium acetate, pH 4.6, 0.1% Triton X-100 and 2 mM DTT. Incubation was performed at room temperature for 24 h, with constant mixing of the gel. 25 μg baculo TRAP or bone TRAP were digested with 100 μl (5units) trypsin-agarose in 500 μl of incubation solution; 10 mM Tris pH 7.0 and 0.1% Triton X-100.

Incubation was performed at room temperature for 1 h with the suspension kept well mixed during the reaction period. The proteolytic digestions above were stopped by centrifugation and the cleavage products of TRAP in the supernatant were further analyzed. Digestion of baculo TRAP or bone TRAP with cathepsin B were performed at (final concentrations); 10 ng TRAP/μl, 0.4 mU cathepsin B/μl, 2 mM DTT, 50 mM sodium acetate and 1 mM EDTA, pH 5.5. The incubations were performed at 37° C. for 24 h and digestions were stopped with protease inhibitor cocktail Complete according to the instructions of the manufacturer.

Purification of Milk OPN

Osteopontin (OPN) was purified from bovine milk essentially as published in [36]. Briefly, 1 liter raw milk was centrifuged for 15 min at 1,250 g and the non-fatty part was mixed with DEAE-Sephacel and rotated over-night at 4° C. Then the mix was first washed by centrifugation with 1.1 liter of 0.2 M NaCl in 10 mM phosphate buffer, pH 7.4 and then with 600 ml of 0.25 M NaCl in the same buffer. The mix was applied to a column and eluted with 0.3 M NaCl in 10 mM phosphate buffer pH 7.4. The protein peak was pooled and adjusted to 4 M NaCl before applied to a Phenyl-Sepharose column (30 ml) (equilibrated with 4 M NaCl in 10 mM phosphate buffer pH 7.4). After wash with 4 M NaCl in 10 mM phosphate buffer pH 7.4 the protein was eluted with 2 M NaCl in the same buffer. The protein peak was pooled, adjusted to 5 M NaCl, and applied to a smaller (5 ml) Phenyl-Sepharose column equilibrated with 5 M NaCl in 10 mM phosphate buffer pH 7.4. After a rigorous wash with equilibration buffer the protein was eluted with 2 M NaCl in 10 mM phosphate buffer pH 7.4. The protein peak was pooled and the elution buffer was replaced with TBS (137 mM NaCl, 2 mM KCl, 25 mM Tris-HCl pH 7.4) by ultrafiltration with an Amicon cell equipped with a YM 10 filter.

Western Blot

SDS-polyacrylamide gel electrophoresis under reducing conditions was performed essentially according to the procedure described by Laemmli [38]. Proteins were blotted onto immuno-PVDF membranes. Colloidal gold was used for protein staining.

Immunoblots were probed with polyclonal antiserum (diluted 1:100) raised in rabbits using rat recombinant TRAP as the immunogen [10] and the secondary antibody was alkaline phosphatase conjugated goat anti-rabbit IgG (diluted 1:500). Development was performed with NBT/BCIP. All operations were carried out according to the protocols of the manufacturers.

Densitometric Analysis

Densitometric analysis of TRAP for purity estimations was performed on Western blots. Blotted membranes were scanned and densitometric analysis of scanned images for purity estimations was performed with Sigma Gel, Gel Analysis Software version 1.05 (Jandel Corporation, Calif.). The band intensity of the proteinstained lanes was coverted by the software to peak heights, and peak areas were calculated. TRAP bands were identified by comparing with immunostained lanes from the same blot. The purity of baculoTRAP and bone TRAP preparations was calculated as the ratio of TRAP peak areas and total protein areas.

N-terminal Amino Acid Sequence Analysis

N-terminal amino acid sequence analysis was carried out by Edman degradation using a Hewlett Packard 1090 sequencer with adsorptive biphasic column technology.

Approximately 20 μg of baculoTRAP digested with papain-agarose were loaded for sequence analysis.

Example 1

Purification of Rat Recombinant and Bone TRAP

The preparations or recombinant (Baculo TRAP) and native rat bone TRAP (Bone TRAP) used in the experiments exhibited a specific activity of around 200 U/mg protein.

Bone TRAP (See FIG. 1, lanes 1 and 2) and BaculoTRAP (See FIG., lanes 3 and 4) were electrophoresed on 12% SDS-polyacrylamide gel under reducing conditions and blotted onto a PVDF membrane.

The figures to the left FIG. 1 denote the positions of molecular weight standards and to the right are the estimated molecular weight sizes of the major TRAP bands (in kDa). Lanes 1 and 3 (1 ug of protein) were proteinstained and lanes 2 and 4 (0.5 ug of protein) were immunostained as described under Materials and Methods.

Results: SDS-PAGE under reducing conditions, electroblotting and staining of blots for protein using Collodial gold (FIG. 1, lane 3) showed one major band corresponding to an Mr of 35 kDa. In a parallell lane, immunostained using a polyclonal antibody generated in rabbits using the purified recombinant rat TRAP as the immunogen, some additional bands were visible. The bands at 20 kDa and 16 kDa correspond to the disulphide-linked fragments contained in the two-subunit form [10]. Bands appearing on the proteinstained blots without a corresponding band on the immunostained neighbouring lane were considered as impurities. From densitometric analysis using the SigmaGel software, the purity of this preparation was estimated to around 90%.

The bone TRAP was purified from long bones of 3-week old rats using essentially the same procedure as for the recombinant TRAP. In this preparation (FIG. 1, lanes 1 and 2), which had a specific activity of 1,165 U/mg protein, an apparent inverse proportion of monomeric and two-subunit forms compared to the recombinant enzyme preparation was noted (FIG. 1, cf lanes 2 and 4). This preparation was considered approximately 40% pure using the densitometric analysis described above.

It was thus found that the TRAP enzyme from rat bone was mainly in the fragmented, two-subunit form and exhibited at least 5–6-fold higher catalytic activity compared to the mostly monomeric species with significantly lower specific activity contained in the recombinant TRAP preparation.

Example 2
Proteolytic Cleavage in vitro of the Monomeric Recombinant TRAP

BaculoTRAP was digested with papain or trypsin and compared with undigested BaculoTRAP and bone TRAP. 150 ng of TRAP was electrophoresed on a 12% SDS-polyacrylamide gel under reducing conditions. The proteins were blotted onto a PVDF membrane and developed as described under Materials and Methods.

FIG. 2. shows the fragmentation pattern after proteolytic digestion of recombinant TRAP. It has been previously demonstrated that the monomeric form of bovine spleen TRAP can be converted to the two-subunit form by limited proteolytic cleavage with either of the serine proteases trypsin or chymotrypsin with a significant increase in enzyme activity [29].

Results: Using trypsin-conjugated agarose beads, a complete conversion of the monomeric recombinant TRAP was achieved with novel bands appearing at 25 and 16 kDa as well as a broad band area between 18–22 kDa (FIG. 2). The cysteine proteinase papain also gave a complete conversion of the monomeric form, but yielded a fragment of Mr 23 kDa together with a broad band area migrating with a slightly lower Mr than that observed after digestion with trypsin. The smaller fragment migrated to the same 16 kDa position irrespective of which protease was used. For a comparison, the bone TRAP preparation contained only the broad band centering at 22 kDa together with the common 16 kDa band. In order to determine the cleavage site(s) N-terminal sequence analysis was performed (data not shown). In the original recombinant TRAP fraction, two N-terminal sequences were detected; the predominant sequence starting with T-A-P-A-S-T, corresponding to amino acid residues 1–6 in the mature protein and a minor sequence V-A-R-T, corresponding to amino acids 161–164 in the deduced protein sequence [9]. In the rat bone TRAP, the 2 N-terminal sequences detected were the A-P-A-S-T and R-T-Q-L-S-W, the latter corresponding to amino acids 163–168 [9].

We have previously noted the discrepancy between the predicted sequence of the mature protein and the actual N-terminal sequence of the purified rat bone enzyme, missing a N-terminal threonine residue [9, 26]. Interestingly, the papain-cleaved recombinant TRAP was cleaved at the $Ala^{162}$–$Arg^{163}$ peptide bond, as present in the TRAP isolated from rat bone.

Example 3
Effects of Proteolytic Cleavage in vitro On TRAP Enzymatic Parameters a) Cleavage of recombinant TRAP with the proteases trypsin and papain was associated with significant enhancement of enzymatic activity using pNPP as the substrate only with papain (See Table I).

This was due both to a 3-fold decrease in the Km for pNPP, as well as an increase in the Kcat. Expressing these changes as the ratio of kcat/Km, a 10-fold increase in this ratio was apparent for the papain-cleaved recombinant TRAP compared to the untreated monomeric TRAP. The kcat/Km ratio was even higher in the papain-cleaved recombinant TRAP preparation compared to the preparation of rat bone TRAP.

TABLE I. Kinetic properties for pNPP hydrolysis of recombinant rat TRAP (BacTRAP), recombinant TRAP treated with proteases and boneTRAP.

Km expressed as mM; kcat/Km as $M^{-1}s^{-1}$.

| BacTRAP | | | | | | | | | BoneTRAP | |
|---|---|---|---|---|---|---|---|---|---|---|
| – | | + trypsin | | + papain | | + Cath. B | | – | |
| Km | Kcat/Km | Km | Kcat/Km | Km | Kcat/Km | Km | Kcat/Km | Km | Kcat/Km |
| 3.1 | $7.3 \cdot 10^4$ | 2.1 | $7.1 \cdot 10^4$ | 1.0 | $8.0 \cdot 10^5$ | 0.9 | $9.0 \cdot 10^5$ | 1.0 | $3.3 \cdot 10^5$ |

This unexpected finding is most likely due to the lower purity of the bone TRAP preparation compared to the recombinant TRAP leading to an under-estimation of the actual specific activity of the rat bone preparation by at least a factor of 2. If corrected in this way, the activities of the papain-cleaved recombinant TRAP and the rat bone TRAP are comparable. In addition to papain, another member of the cysteine proteinase family, cathepsin B, was able to activate the recombinant TRAP to a similar extent as papain. Trypsin, on the other hand, was without stimulatory effect in this regard.

b) The activity of BaculoTRAP digested with papain or trypsin was compared with undigested baculoTRAP and bone TRAP at different pH. TRAP activity was measured with pNPP as the substrate as described under Materials and Methods.

pH-dependence for pNPP hydrolysis of intact and proteolytically cleaved TRAP is shown in FIG. 3.

The TRAPs usually exhibit a pH-optimum for hydrolysis of phosphomonoesters in the range of 5.5–6.0 [39]. The recombinant TRAP as isolated exhibited a rather broad pH-optimum between 4.5–5.0, i.e by 1 pH unit lower than the rat bone TRAP (FIG. 3).

Interestingly, cleaving the monomeric recombinant TRAP with papain as well as trypsin caused a shift in the optimal pH of pNPP hydrolysis to more basic pH-values, for trypsin 5.0–5.5 and for papain 5.5–6.0. This suggests that protonation reactions in amino acid residues involved in catalysis are affected, presumably by conformational changes induced by limited proteolytic cleavage.

c) BaculoTRAP digested with papain or trypsin were compared with undigested baculoTRAP and bone TRAP. Ascorbic acid and $FeCl_3$ were used as reducing agents during preincubation of TRAP for indicated time intervals in a total volume of 70 μl with (final concentrations); 1 mM ascorbic acid, 0.1 mM $FeCl_3$, 0.15 M KCl, 10 mM sodium tartrate, 0.1% Triton X-100. Except for a substrate incubation time of 10 min, TRAP activity was measured after the addition of 80 μl of substrate solution as described under Materials and Methods.

Figure 4B:
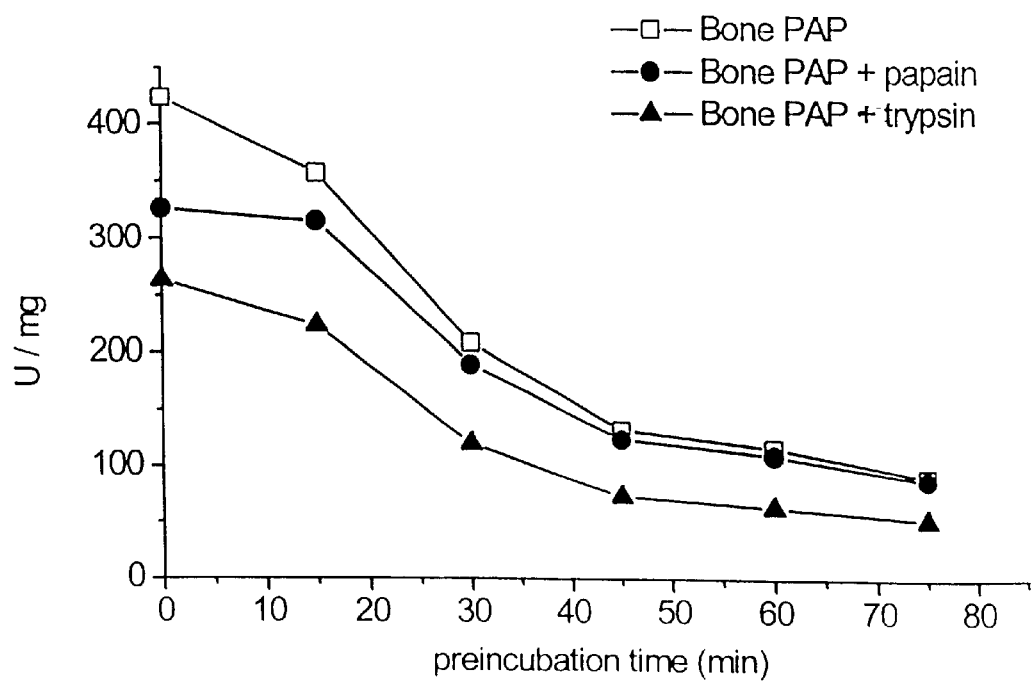

The differential sensitivity of intact and proteolytically cleaved TRAP to reducing agents is shown in FIG. 4.

Result: The di-iron containing TRAPs are redox-sensitive enzymes, due to a redox-active M2 site when present as the ferrous ion yields a catalytically active enzyme [3].

Consequently, in an oxygen environment the TRAPs are present in an inactive diferric form, which can be rapidly activated by addition of reducing agents such as ascorbate.

Following a maximal activation within 10 minutes, it was observed (FIG. 4b) that prolonged pre-incubation with ascorbate (1 mM) in the presence of 0.1 mM FeCl, led to a time-dependent inactivation of the rat bone TRAP. This could be due to a conversion of the mixed-valent active enzyme to an inactive Fe(II)Fe(II) species [40]. However, although the intact recombinant TRAP did not show this tendency for inactivation under the same conditions (FIG. 4a), digestion with papain resulted in a similar response as for the native bone TRAP enzyme. This could be interpreted that proteolytic cleavage with papain and related members of this superfamily induce structural changes in the TRAP molecule which affects the redox-sensitivity of the di-iron metallic center. It is tempting to that endogenous cysteine proteinases such as cathepsin B are involved in redox-dependent regulation of TRAP activity in the biologically relevant TRAP from rat bone.

Example 4
Substrate Specificities of Rat Recombinant TRAP and Bone TRAP

In order to validate whether the structural alterations induced by proteolytic cleavage of the monomeric TRAP was generally affecting known substrates for TRAP and not restricted to the non-physiological substrate pNPP, we surveyed a number of different phosphoaminoacids, phosphopeptides and the phosphoprotein osteopontin as substrates for the TRAPs (See Table II).

TABLE II

Substrate specificity of recombinant rat TRAP produced using Baculovirus expression system (BacTRAP) compared to TRAP isolated from rat bone (BoneTRAP). Expressed as Kcat/Km ($M^{-1} \cdot s^{-1}$)

|  | BacTRAP | Ratio | BoneTRAP | Ratio | Ratio Bone/Bac |
|---|---|---|---|---|---|
| pT | $0.8 \cdot 10^2$ | 1.0 | $1.1 \cdot 10^3$ | 1.0 | 14 |
| pS | $1.0 \cdot 10^2$ | 1.2 | $2.2 \cdot 10^3$ | 2.0 | 22 |
| RRA(pT)VA | $2.2 \cdot 10^2$ | 2.8 | $1.1 \cdot 10^3$ | 10 | 5.0 |
| FRI(pS)HELDS | $1.1 \cdot 10^3$ | 14 | $1.7 \cdot 10^4$ | 15 | 15 |
| EDEE(pS)EDEE | $4.0 \cdot 10^3$ | 50 | $1.7 \cdot 10^4$ | 15 | 4.2 |
| pY | $2.0 \cdot 10^4$ | 250 | $3.9 \cdot 10^5$ | 350 | 19 |
| END(pY)INASL | $3.0 \cdot 10^4$ | 375 | $3.1 \cdot 10^5$ | 280 | 10 |
| DADE(pY)LIPQQG | $3.8 \cdot 10^4$ | 475 | $7.0 \cdot 10^5$ | 640 | 18 |
| pNPP | $8.6 \cdot 10^4$ | 1075 | $7.6 \cdot 10^5$ | 690 | 8.8 |
| OPN | $1.5 \cdot 10^5$ | 1875 | $2.6 \cdot 10^6$ | 2360 | 17 |

Result: Among the phosphoaminoacids. both phosphoserine and phosphothreonine were poor substrates for both forms of TRAPs, with kcat/Km values in the range of $10^2$–$10^3$. A similar value was observed with the phospho-threonyl peptide RRA(pT)VA, containing the consensus sequence for protein kinase A [41]. The acidic phospho-seryl peptide EDEE(pS)EDEE with the consensus sequence for casein kinase II [42] as well as the OPN peptide FRI(pS)HELDS [43, 44] was slightly more effective substrates. On the other hand, phosphotyrosine and two different phosphotyrosyl peptides were equally effective as pNPP as substrates with the Kcat/Km ratio between $10^4$–$10^5$. However, the most effective of all substrates tested was the acidic phospho-seryl protein osteopontin from bovine milk. For all substrates, the rat bone enzyme was more active, varying for different substrates between 4 to 19-fold higher compared to the recombinant TRAP.

Example 5
High Throughput Screen Using Recombinant TRAP

The assay measured the conversion of para-nitrophenyl Phosphate (pNPP) to paranitrophenol (pNP) by TRAP in the presence of test compounds. 84073 compounds were tested. In initial single assays at 50 uM were conducted and 1012 compounds inhibited TRAP activity by 30% or better. Retests of these compounds in duplicates showed 301 compounds remaining at 30% or better inhibition of TRAP activity. 284 of the 301 compounds were evaluated in a confirmation assay rendering 217 reproducible, confirmed active TRAP inhibitors.

REFERENCES

1 Antanaitis, B. C. et al. (1983) Adv. Inorg. Biochem. 5, 111–136
2 Averill, B. A., et al (1987) J. Am. Chem. Soc. 109, 3760–3767
3 Doi, K et al (1988) Struct. Bond. 70, 1–26
4 Vincent, J. B. et al (1990) FASEB J. 4, 3009–3014
5 Andersson, G et al (1991) Acid phosphatases, CRC Press, Boca Raton
6 Cassady, A. I., et al (1993) Gene 130, 201–207
7 Ketcham, C. M et al (1989) J. Biol. Chem. 264, 557–563
8 Lord, D. K et al (1990) Eur. J. Biochem. 189, 287–293
9 Ek-Rylander, B et al. (1991) J. Biol. Chem. 266, 24684–24689
10 Ek-Rylander, B et al (1997) Biochem. J. 321, 305–311
11 Beck, J. L et al (1988) J. Am. Chem. Soc. 110, 3317
12 Griffith, J. P et al (1995) Cell 82, 507–522
13 Goldberg, J et al (1995) Nature 376, 745–753
14 Andersson, G et al. (1989) Connect. Tissue Res. 20, 151–158
15 Andersson, G. et al. (1995) Acta Orthop. Scand. 66, 189–194
16 Ek-Rylander, B et al (1994) J. Biol. Chem. 269, 14853–14856
17 Marshall, K et al (1997) Arch. Biochem. Biophys. 345, 230–236
18 Janckila, A. J., et al (1992) Leukemia 6, 199–203
19 Robinson, D. B. et al. (1981) Arch. Biochem. Biophys. 210, 186–199
20 Schindelmeiser, J et al (1987) Histochemistry 87, 13–19
21 Schindelmeiser, J et al (1989) Histochemistry 92, 81–85
22 Andersson, G. N. et al (1989) J. Histochem. Cytochem. 37, 115–117
23 Yaziji, H et at (1995) Am. J. Clin. Pathol. 104, 397–402
24 Hayman, A. R et al. (1991) Biochem. J. 277, 631–634
25 Halleen, J et al. (1996) J. Bone Miner. Res. 11, 1444–1452
26 Ek-Rylander, B et al (1991) J. Bone Miner. Res. 6, 365–373
27 Hayman, A. R et al (1989) Biochem. J. 261, 601–609
28 Ketcham, C. M., et al (1985) J. Biol. Chem. 260, 5768–5776
29 Orlando, J. L et al. (1993) Biochemistry 32, 8120–8129
30 Robinson, D. B et al (1980) J. Biol. Chem. 255, 5864–5870
31 Ling, P. et al. (1993) J. Biol. Chem. 268, 6896–6902
32 Hayman, A. R. et al. (1994) J. Biol. Chem. 269, 1294–1300
33 Everts, V et al. (1998) J. Bone Miner. Res. 13, 1420–1430
34 Hill, P. A et al (1994) J. Cell. Biochemistry 56, 118–130
35 Lerner, U. H et al A. (1997) Acta Physiol. Scand. 161, 81–92
36 Bayless, K. J et al (1997) Protein Expression and Purification 9, 309–314

37 Baykov, A. A et al. (1988) Anal. Biochem. 171, 266–270
38 Laemmli, U. K. (1970) Nature 227, 680–685
39 Andersson, G et al. (1984) Arch. Biochem. Biophys. 228, 431–438
40 Beck, J. L et al. (1984) Biochim. Biophys. Acta 791, #357–363
41 Pinna, L. A et al. (1996) Biochem. Biophys. Acta. 1314, 191–225
42 Songyang, Z et al. (1996) Mol. Cell. Biol. 16, 6486–6493
43 Salih, E et al. (1997) J. Biol. Chem. 272, 13966–13973
44 Sörensen. E. S et al. (1995) Protein Sci. 4, 2040–2049

What is claimed is:

1. A method for identifying a compound that inhibits tartrate-resistant and purple acid phosphatase (TRAP) activity, comprising:
   a) obtaining activated TRAP by activation of TRAP with a cysteine proteinase,
   b) contacting a test compound with the activated TRAP, and
   c) measuring dephosphorylation of a substrate by the activated TRAP in the presence of the test compound,
   whereby a compound that decreases the dephosphorylation of the substrate by the activated TRAP, relative to dephosphorylation of the substrate by activated TRAP in the absence of the test compound, is identified as a compound that inhibits TRAP activity.

2. A method for screening for inhibitors of tartrate-resistant and purple acid phosphatase (TRAP) activity, comprising contacting a test compound with activated TRAP and measuring dephosphorylation of a phosphorylated peptide or protein substrate by the activated TRAP contacted with the test compound, wherein a test compound that decreases the dephosphorylation of the phosphorylated peptide or protein substrate by the activated TRAP, relative to dephosphorylation of the phosphorylated peptide or protein substrate by activated TRAP in the absence of the test compound, is identified as a substance which inhibits TRAP activity; wherein the activated TRAP is formed by reacting TRAP with a cysteine proteinase.

3. The method according to claim 2, comprising producing TRAP by recombinant methods.

4. The method according to claim 2, wherein the cysteine proteinase is cathepsin.

5. The method according to claim 4, wherein the cathepsin is cathepsin B.

6. The method according to claim 2, comprising measuring dephosphorylation of a phosphoprotein comprising a moiety selected from the group consisting of a phosphotyrosyl moiety, a phosphoseryl moiety, and mixtures thereof.

7. The method according to claim 6, wherein the activated TRAP protein is of osteoclast origin.

8. The method according to claim 2, comprising measuring dephosphorylation of a bone matrix protein.

9. A method according to claim 1, comprising producing by recombinant methods the TRAP used in the activation step (a).

10. A method according to claim 9, wherein the cysteine proteinase is selected from the group consisting of papain, cathepsin and mixtures thereof.

11. A method according to claim 9, wherein the activated recombinant TRAP is formed by cleaving recombinant TRAP at an Ala—Arg peptide bond.

12. A method according to claim 1, wherein the TRAP is rat or human TRAP.

13. A method according to claim 2, wherein the TRAP is rat or human TRAP.

14. A method according to claim 1, wherein the cysteine proteinase is selected from the group consisting of papain, cathepsin and mixtures thereof.

15. A method according to claim 2, wherein the cysteine proteinase is selected from the group consisting of papain, cathepsin and mixtures thereof.

16. A method according to claim 8, wherein the bone matrix protein comprises osteopontin or bone sialoprotein.

* * * * *

UNITED STATES PATENT AND TRADEMARK OFFICE
CERTIFICATE OF CORRECTION

PATENT NO. : 6,451,548 B1
DATED : September 17, 2002
INVENTOR(S) : Gordan Andersson, Barbro Ek-Rylander and Corenlia Oellig It is certified that error appears in the above-identified patent and that said Letters Patent is hereby corrected as shown below:

Title page,
Item [30], Foreign Application Priority Data, after "9803959" add -- -7 --
Item [56], References Cited, OTHER PUBLICATIONS, "Primer on the Metabolic…" reference, after "Metabolic" insert -- Bone --

Column 2,
Line 47, replace "kIDa" with -- kDa --
Line 54, replace "reduce" with -- reduces --

Column 3,
Line 17, replace "cystein" with -- cysteine --
Line 48, after "disorders," insert -- and --

Column 4,
Line 17, replace "(PS)" with -- (pS) --
Line 37, after "U/mg" insert -- protein, which gradually dropped during prolonged storage at -80ºC. --

Column 5,
Line 12, replace "(0-nmol)" with -- (0-2 nmol) --
Line 17, replace "100 pl (0 7 units)" with -- 100 µl (0.7 units) --

Column 6,
Line 27, replace "or" with -- of --
Line 31, insert -- 1 -- between "Fig." and ","
Line 34, after "left" insert -- in --

Column 9,
Line 17, delete "tempting to" and insert -- believed --
Line 51, before "both" replace "." with -- , --

UNITED STATES PATENT AND TRADEMARK OFFICE
CERTIFICATE OF CORRECTION

PATENT NO. : 6,451,548 B1
DATED : September 17, 2002
INVENTOR(S) : Gordan Andersson, Barbro Ek-Rylander and Corenlia Oellig It is certified that error appears in the above-identified patent and that said Letters Patent is hereby corrected as shown below:

Column 11,
Line 11, after "Sörensen" delete "." and insert -- , --

Signed and Sealed this

Tenth Day of August, 2004

JON W. DUDAS
*Acting Director of the United States Patent and Trademark Office*